(12) United States Patent
Wasserkrug et al.

(10) Patent No.: US 12,093,848 B2
(45) Date of Patent: Sep. 17, 2024

(54) LEARNING PARAMETERS OF BAYESIAN NETWORK USING UNCERTAIN EVIDENCE

(71) Applicant: International Business Machines Corporation, Armonk, NY (US)

(72) Inventors: Eliezer Segev Wasserkrug, Haifa (IL); Radu Marinescu, Dublin (IE)

(73) Assignee: International Business machines Corporation, Armonk, NY (US)

( * ) Notice: Subject to any disclaimer, the term of this patent is extended or adjusted under 35 U.S.C. 154(b) by 960 days.

(21) Appl. No.: 17/107,984

(22) Filed: Dec. 1, 2020

(65) Prior Publication Data

US 2022/0172091 A1 Jun. 2, 2022

(51) Int. Cl.
  *G06N 7/02* (2006.01)
  *G06N 7/01* (2023.01)
  *G06N 20/00* (2019.01)

(52) U.S. Cl.
  CPC .............. *G06N 7/02* (2013.01); *G06N 7/01* (2023.01); *G06N 20/00* (2019.01)

(58) Field of Classification Search
  None
  See application file for complete search history.

(56) References Cited

U.S. PATENT DOCUMENTS 6,415,276 B1 * 7/2002 Heger ..................... G05B 9/02
  702/183
2004/0220892 A1 11/2004 Cohen
2009/0313204 A1 * 12/2009 Van Zon ................. G06N 7/01
  706/52
2012/0078678 A1 * 3/2012 Pradhan ............. G06Q 10/0633
  705/7.27

OTHER PUBLICATIONS

Bornhold et al., Uncertain<T>: A First-Order Type for Uncertain Data, ASPLOS '14, Mar. 1-5, 2014, Total pp. 15 (Year: 2014).*
Ben Mrad et al. "An Explication of Uncertain Evidence in Bayesian Networks: Likelihood Evidence and Probabilistic Evidence," Applied Intelligence 1-23, 2015.
Ben Mrad et al. "Uncertain Evidence in Bayesian Networks : Presentation and Comparison on a Simple Example," IPMU 2012, Part III, CCIS 299, pp. 39-48, 2012.

(Continued)

Primary Examiner — Alan Chen
(74) Attorney, Agent, or Firm — Stosch Sabo

(57) ABSTRACT

A method, system, and computer program product for learning parameters of Bayesian network using uncertain evidence, the method comprising: receiving input comprising graph representation and at least one sample of a Bayesian network, the graph comprising plurality of nodes representing random variables and plurality of directed edges representing conditional dependencies, wherein each of the at least one sample comprising for each node a value selected from the group consisting of: a known value; an unknown value; and an uncertain value; and applying on the input a Bayesian network learning process configured for calculating estimates of conditional probability tables of the Bayesian network using probabilities inferred by applying on the input a Bayesian network uncertain inference process configured for performing inference in a Bayesian network from uncertain evidence.

21 Claims, 4 Drawing Sheets

(56) References Cited

OTHER PUBLICATIONS

Choi et al. "EDML: A Method for Learning Parameters in Bayesian Networks," Conference: UAI 2011, Proceedings of the Twenty-Seventh Conference on Uncertainty in Artificial Intelligence, Barcelona, Spain, Jul. 14-17, 2011: 115-124.

Masegosa et al. "Learning from Incomplete Data in Bayesian Networks with Qualitative Influences," International Journal of Approximate Reasoning 69: 18-34, 2016.

Wistuba et al. "Scalable Multi-Class Bayesian Support Vector Machines for Structured and Unstructured Data," arXiv:1806.02659v1 [cs.LG] Jun. 7, 2018, 14 pages.

\* cited by examiner

| Dyspnoea? | | | | |
|---|---|---|---|---|
| Bronchitis? | yes | | no | |
| Tuberculosis or Cancer? | yes | no | yes | no |
| yes | 0.9 | 0.8 | 0.7 | 0.1 |
| no | 0.1 | 0.2 | 0.3 | 0.9 |

| DyspnoeaObs | | |
|---|---|---|
| Dyspnoea? | yes | no |
| False | 0.3 | 0.7 |
| True | 0.7 | 0.3 |

Require: Bayesian network $\mathcal{B} = \langle \mathbf{X}, \mathbf{D}, G, P \rangle$, dataset $S$
1: procedure EM($\mathcal{B}, S$)
2:    Initialize $\mathcal{B}$'s parameters $\theta \leftarrow \theta^0$
3:    for all $t = 1, \ldots,$ until convergence do
4:       $\{M_{\theta^t}[x_i, u_i]\} \leftarrow$ COMPUTE-ESS($\mathcal{B} = (G, \theta^t), S$)
5:       for all $i = 1, \ldots, n$ do
6:          for all $x_i, u_i \in Val(X_i, Pa^{\mathcal{B}}_{X_i})$ do
7:             $\theta^{t+1}_{x_i|u_i} = \frac{M_{\theta^t}[x_i, u_i]}{M_{\theta^t}[u_i]}$
8:          end for
9:       end for
10:    end for
11: end procedure
12: function COMPUTE-ESS($\mathcal{B} = (G, \theta), S$)
13:    for all $i \in 1, \ldots, n$ do
14:       for all $x_i, u_i \in Val(X_i, Pa^{\mathcal{B}}_{X_i})$ do
15:          $M[x_i, u_i] \leftarrow 0$
16:       end for
17:    end for
18:    for all example $S_j \in S$ do
19:       Let $O_j$ be the observations induced by $S_j$
20:       $(G', \theta') \leftarrow$ AUGMENT-BN($\mathcal{B} = (G, \theta), O_j$)
21:       for all $o \in O_j$ do
22:          Set the value of $o_V$ to $true$
23:       end for
24:       Run inference on $(G', \theta')$ with evidence $d_j$
25:       for all $i = 1, \ldots, n$ do
26:          for all $x_i, u_i \in Val(X_i, Pa^{\mathcal{B}}_{X_i})$ do
27:             $M[x_i, u_i] \mathrel{+}= P_{(G', \theta')}(x_i, u_i | d_j)$
28:          end for
29:       end for
30:    end for
31: end function
32: function AUGMENT-BN($\mathcal{B} = (G, \theta), O$)
33:    Initialize $G' \leftarrow G, \theta' \leftarrow \theta$
34:    for all $o \in O$ do
35:       $G'_V \leftarrow G'_V \cup O_V, G'_E \leftarrow G'_E \cup (V, o_V)$   ▷ Add a new observation node to the graph and connect it to the relevant node
36:       for all $c_i \in Conf$ do
37:          $\theta' \leftarrow \theta' \cup \theta_{O_V = true | v_i} = c_i$   ▷ Set the relevant CPT entry to be $Pr(obs|V = v_i)$
38:       end for
39:    end for
40:    return $(G', \theta')$
41: end function

FIG. 4

LEARNING PARAMETERS OF BAYESIAN NETWORK USING UNCERTAIN EVIDENCE

BACKGROUND

Some embodiments described in the present disclosure relate to data analysis and, more specifically, but not exclusively, to learning parameters of Bayesian network using uncertain evidence.

Bayesian networks are a type of probabilistic graphical model used for representing probabilistic relationships among a large number of variables. Bayesian networks aim to model conditional dependence, and sometimes causation, by representing conditional dependence through the structure of a directed graph. Through these relationships, one can conduct inference on the random variables represented by nodes in the graph, using factorized form representation of their joint probability distribution. Bayesian networks provide a powerful way to embed knowledge and to update one's beliefs about target variables given new information about other variables. They are widely used for an ample range of tasks including prediction, classification, anomaly detection, diagnostics, automated insight, reasoning, time series prediction and decision making under uncertainty.

In a Bayesian network, prior knowledge is represented by a probability distribution P on the set of variables which define the problem, whereas updated beliefs are represented by the posterior probability distribution P(·|obs) where obs represents new information. Inference in Bayesian networks provides a means to update the probability space over the variables given the observations. Examples of inference include Maximum A Posteriori Assignment (MAP), Most Probable Explanation (MPE), and Most Relevant Explanation (MRE). Evidence is the starting point of such methods and refers to new information in a Bayesian network. A piece of evidence is also called a finding or an observation, and evidence refers to a set of findings.

A finding on a variable commonly refers to an instantiation of the variable. This can be represented by a vector with one element equal to 1, corresponding to the state the variable is in, and all other elements equal to zero. This type of evidence is usually referred to as hard evidence. Another type of evidence, that cannot be represented by such vectors, is uncertain evidence. In a publication entitled "An explication of uncertain evidence in Bayesian networks: likelihood evidence and probabilistic evidence" by A. B. Mrad et al. in *Applied Intelligence* 43(4): 802-824. ISSN 0924-669X. doi:10.1007/s10489-015-0678-6. doi.org/10.1007/s10489-015-0678-6 (hereinafter "Mrad et al."), the contents of which being incorporated herein in the entirety by reference without giving rise to disavowal, the authors identify several exemplary types or categories of uncertain evidence, including likelihood evidence, probabilistic evidence (fixed or not-fixed), and/or the like, as well as techniques and/or tools for performing inference incorporating uncertain evidence of this sort.

SUMMARY

It is an object of the present disclosure to describe a system and a method for learning parameters of Bayesian network using uncertain evidence.

The foregoing and other objects are achieved by the features of the independent claims. Further implementation forms are apparent from the dependent claims, the description and the figures.

According to an aspect of some embodiments of the disclosed subject matter, there is provided a method for learning parameters of Bayesian network from uncertain evidence, comprising: receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value; and applying on the input a Bayesian network learning process configured for calculating estimates of conditional probability tables of the Bayesian network using probabilities of random variables represented by the plurality of nodes, which probabilities being inferred by applying on the input a Bayesian network uncertain inference process configured for performing inference in a Bayesian network from uncertain evidence comprising one or more uncertain values in one or more samples.

Optionally, for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; and a likelihood ratio comprising quantitative representation of a conditional probability of an observed value of the node in the sample for each value in a domain of possible values of the node.

Optionally, the Bayesian network uncertain inference process being further configured for obtaining an augmented Bayesian network by adding a child node and corresponding conditional probability table for each node of the at least one node being associated with a likelihood ratio, the child node representing a binary random variable of whether for the node the uncertain value being observed in the sample, the corresponding conditional probability table comprising probabilities obtained from the likelihood ratio, and wherein the uncertain Bayesian network inference process being further configured for performing inference using the augmented Bayesian network and known values of the sample.

Optionally, the Bayesian network uncertain inference process being further configured for completing a sample comprising at least one unknown value by calculating a statistic for each node for which the value thereof in the sample being unknown.

Optionally, the Bayesian network learning process being further configured for iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

Optionally, the Bayesian network learning process being further configured for performing continuous learning by calculating and saving a number of samples used for calculating each of at least one probability distribution entry in a conditional probability table of the Bayesian network, and updating each of the at least one probability distribution entry using the number of samples saved.

Optionally, the Bayesian network learning process being further configured for incorporating expert estimates.

According to another aspect of some embodiments of the disclosed subject matter, there is provided a computer program product comprising: a non-transitory computer readable storage medium; program instructions for executing, by a processor, a method for learning parameters of Bayesian network from uncertain evidence, the method comprising: receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value; and applying on the input a Bayesian network learning process configured for calculating estimates of conditional probability tables of the Bayesian network using probabilities of random variables represented by the plurality of nodes, which probabilities being inferred by applying on the input a Bayesian network uncertain inference process configured for performing inference in a Bayesian network from uncertain evidence comprising one or more uncertain values in one or more samples.

Optionally, for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; and a likelihood ratio comprising quantitative representation of a conditional probability of an observed value of the node in the sample for each value in a domain of possible values of the node.

Optionally, the Bayesian network uncertain inference process being further configured for obtaining an augmented Bayesian network by adding a child node and corresponding conditional probability table for each node of the at least one node being associated with a likelihood ratio, the child node representing a binary random variable of whether for the node the uncertain value being observed in the sample, the corresponding conditional probability table comprising probabilities obtained from the likelihood ratio, and wherein the uncertain Bayesian network inference process being further configured for performing inference using the augmented Bayesian network and known values of the sample.

Optionally, the Bayesian network uncertain inference process being further configured for completing a sample comprising at least one unknown value by calculating a statistic for each node for which the value thereof in the sample being unknown.

Optionally, the Bayesian network learning process being further configured for iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

Optionally, the Bayesian network learning process being further configured for performing continuous learning by calculating and saving a number of samples used for calculating each of at least one probability distribution entry in a conditional probability table of the Bayesian network, and updating each of the at least one probability distribution entry using the number of samples saved.

Optionally, the Bayesian network learning process being further configured for incorporating expert estimates.

According to yet another aspect of some embodiments of the disclosed subject matter, there is provided a system for learning parameters of Bayesian network from uncertain evidence, comprising: a processing circuitry adapted to execute a code for: receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value; and applying on the input a Bayesian network learning process configured for calculating estimates of conditional probability tables of the Bayesian network using probabilities of random variables represented by the plurality of nodes, which probabilities being inferred by applying on the input a Bayesian network uncertain inference process configured for performing inference in a Bayesian network from uncertain evidence comprising one or more uncertain values in one or more samples.

Optionally, for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; and a likelihood ratio comprising quantitative representation of a conditional probability of an observed value of the node in the sample for each value in a domain of possible values of the node.

Optionally, the Bayesian network uncertain inference process being further configured for obtaining an augmented Bayesian network by adding a child node and corresponding conditional probability table for each node of the at least one node being associated with a likelihood ratio, the child node representing a binary random variable of whether for the node the uncertain value being observed in the sample, the corresponding conditional probability table comprising probabilities obtained from the likelihood ratio, and wherein the uncertain Bayesian network inference process being further configured for performing inference using the augmented Bayesian network and known values of the sample.

Optionally, the Bayesian network uncertain inference process being further configured for completing a sample comprising at least one unknown value by calculating a statistic for each node for which the value thereof in the sample being unknown.

Optionally, the Bayesian network learning process being further configured for iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

Optionally, the Bayesian network learning process being further configured for performing continuous learning by calculating and saving a number of samples used for calculating each of at least one probability distribution entry in a conditional probability table of the Bayesian network, and updating each of the at least one probability distribution entry using the number of samples saved.

Optionally, the Bayesian network learning process being further configured for incorporating expert estimates.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which embodiments. Although methods and materials similar or equivalent to those described herein can be used in the practice or testing of embodiments, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments are herein described, by way of example only, with reference to the accompanying drawings. With specific reference now to the drawings in detail, it is stressed that the particulars shown are by way of example and for purposes of illustrative discussion of embodiments. In this regard, the description taken with the drawings makes apparent to those skilled in the art how embodiments may be practiced.

In the drawings:

FIG. 4 is a pseudo-code of an exemplary Expectation-Maximization algorithm for learning parameters of a Bayesian network using likelihood evidence.

DETAILED DESCRIPTION

Figures 1A, 1B:
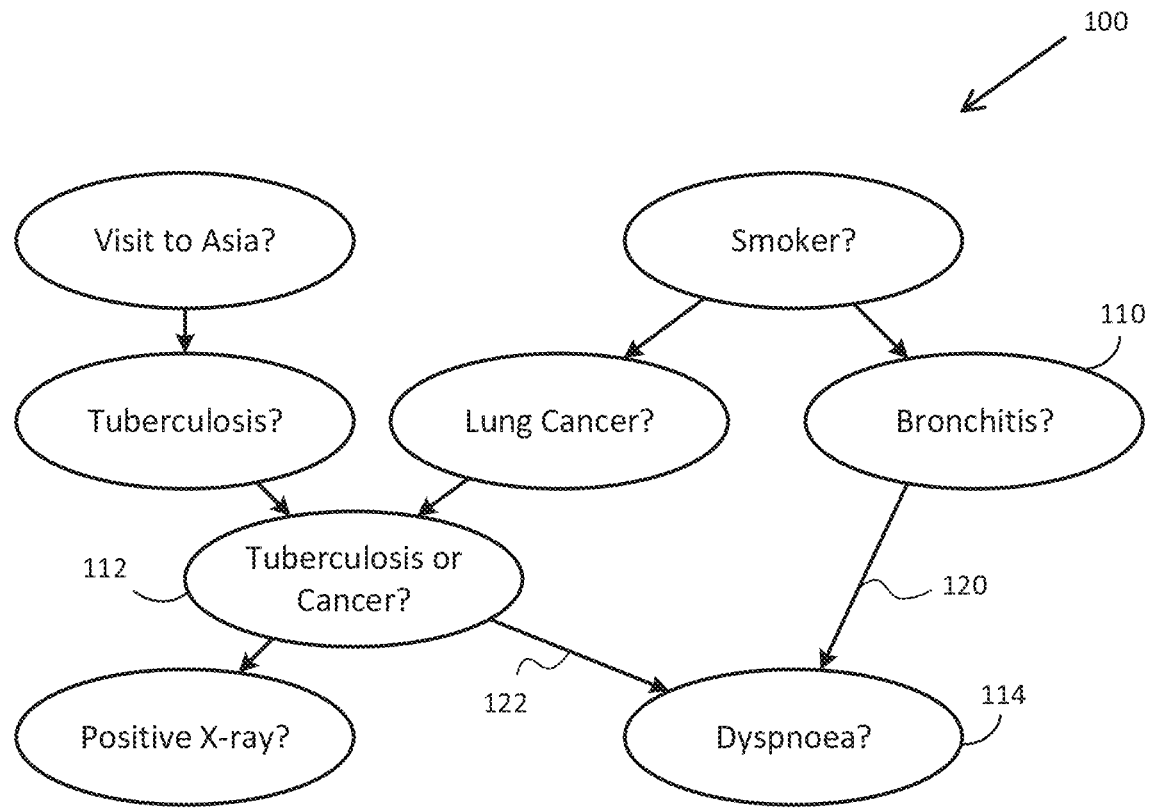
FIG. 1A is a schematic illustration of an exemplary Bayesian network, according to some embodiments.
FIG. 1B is a diagram of an exemplary conditional probability table of a node in a Bayesian network, according to some embodiments.

Some embodiments described in the present disclosure relate to data analysis and, more specifically, but not exclusively, to learning parameters of Bayesian network given uncertain evidence.

Bayesian Networks (BNs) provide a powerful framework for reasoning about conditional dependency structures over many variables. In practice, however, the creation of BNs often requires the specification of a large number of parameters, making it highly desirable to be able to learn these parameters from historical data. In many cases, such data has uncertainty associated with it, including cases in which this data comes from unstructured analysis or from sensors.

When creating diagnosis networks, for example, unstructured analysis algorithms can be run on the historical text descriptions or images of previous cases so as to extract data that can be used for Bayesian Network parameter learning, but such derived data has inherent uncertainty associated with it due to the nature of such algorithms Because of the inability of current Bayesian Network parameter learning algorithms to incorporate such uncertainty, common approaches either ignore this uncertainty, thus reducing the resulting accuracy, or completely disregard such data.

In more detail, an illustrative exemplary real-world application may entail creating a model for electrical equipment diagnosis, in which much of the data available to train the BN was in textual descriptions written by technicians. In order to be able to utilize this data to train the BN, natural language processing (NLP) tools can be used to transform the unstructured data into a structured format more suitable for BN parameter learning. Of course, such natural-language processing models are not completely accurate, and have both false positives and false negatives. In addition, most such tools provide confidence measures indicating their level of certainty about the outcome. It is of course desirable to use such confidence levels when learning the probabilities of the BN.

While there are standard ways to incorporate uncertainty during inference in BNs, incorporating uncertainty of any sort during the parameters' learning has not been addressed.

One technical problem dealt with by the disclosed subject matter is to learn parameters of a Bayesian network from data containing uncertain evidence.

Another technical problem dealt with by the disclosed subject matter is to harness and employ capabilities of Bayesian network inference from uncertain evidence in service of parameter learning, thus allowing incorporating knowledge gained by uncertainty inference into the learning process.

According to some embodiments of the disclosed subject matter, an input comprising graph representation and at least one sample of a Bayesian network (BN) may be received, wherein random variables and conditional dependencies there-among are represented by nodes and directed edges of the graph respectively, and wherein each sample comprising either a known, unknown, or uncertain value for each random variable represented by the BN nodes. A learning process for estimating conditional probability tables (CPTs) of Bayesian network, using Bayesian network inference and resulting probabilities of random variables represented by the BN for calculating estimates of the CPTs, may be employed on the input, wherein in case where uncertain evidence being encountered, the learning process may employ a BN inference process configured for performing inference with uncertain evidence of such sort.

According to some embodiments, a variable X represented by a node of the BN with an observed uncertain value o in a given sample and domain of k possible values, may be associated with a likelihood ratio $L(X)=L(X=x_1): \ldots : L(X=x_k)$ where, when normalized, $L(X=x_1)$ may represent the probability $P(o|X=x_1)$ of the observation of value o occurring when the value or state of X is $x_i$. This may be referred to as a likelihood finding on the variable X, whereas a set of likelihood findings on variables of the BN may be referred to as likelihood evidence. A likelihood finding on a variable in general may be an observation with uncertainty of the variable.

As an illustrative example, consider a Boolean variable node of "Power Failure" in a BN model for electrical equipment diagnosis. Likelihood evidence for the node may be (0.3,0.7) indicating that the confidence associated with the value being true is 0.7 and that it is false is 0.3.

As can readily be appreciated by a person skilled in the art, this type of uncertainty may be suitable for handling the confidence output by unstructured analysis algorithms, sensors, and/or any likewise data source which uncertainty of the observation may originate or result therefrom, for example, due to the unreliability or imprecision of the data source. This is so because likelihood evidence is assumed not to incorporate any prior knowledge beyond what appears directly in the information source (the sensor, text or picture).

According to some embodiments, whenever a likelihood finding on a variable of a node on the BN being encountered in the input, i.e. one or more samples comprise nodes with uncertain values and each being associated with a likelihood ratio an augmented BN may be generated from the graph input by adding an auxiliary binary child node for each of which nodes, and corresponding conditional probability tables may be populated for each respective edge connecting such child node with its parent node. The child node may represent a binary random variable of the uncertain value being observed in a sample of the BN. The augmented BN may then be used for inference from the uncertain evidence, wherein known values in the sample and observations of uncertain values may be treated as certain evidence in the augmented BN, whereas unknown values in the sample and values of nodes for which likelihood ratios being specified may be treated as being unknown, i.e. variables for which no evidence being available. Entries of conditional probability tables of the auxiliary child nodes may comprise respective probabilities of the observed uncertain values occurring conditioned on which value or state, out of all possibilities, the parent nodes being in.

In some embodiments, the learning process may be based on or extend an Expectation-Maximization (EM) algorithm, to enable learning BN parameters that have uncertain evidence associated with them. The EM algorithm in its standard basic form is intended to enable learning of a BN's parameters with missing data, i.e., on examples for which some of the values of the variables in the network are missing or unknown. To do this, it repeats two steps: an expectation step, in which, for each example, the missing data values are replaced with the expected values given the current BN parameters using BN inference; and a maximization step, in which the maximum likelihood values of the BN's parameters are calculated given the (now complete) data. At a high level, this algorithm can be described as follows:

Repeat Until Convergence:
1. Complete the data for each example by calculating the expected value for each variable with missing values given the current parameters of the BN.
2. Update the parameters of the BN to the Maximum Likelihood Estimate (MLE) given the set of full data provided by the expectation step.

In contrast to the case of missing evidence, which may be used when there is missing knowledge about the values of some random variables, uncertain evidence may usually be introduced whenever there is knowledge about the value of the random variable, but the observational process is unable to clearly report a single state for the observed variable.

According to some embodiments, the learning process may be an EM-based learning process in which the standard expectation step being replaced by one that incorporates uncertain evidence propagation into the BN inference.

In some exemplary embodiments, the uncertain evidence may be likelihood evidence and step 1 may be replaced by the following:
1. Complete the data for each example:
   (a) Extend the original network by adding nodes and edges to each node for which there is likelihood evidence, as well as the appropriate conditional probability tables (CPTs). (In this way, the example with likelihood evidence can be replaced with a new example with only missing data. For example, if an observation child has been added to node V, the node V now has an unknown value in this new augmented data point.)
   (b) Calculate the expected value for the nodes with the missing data.

As can readily be appreciated by a person skilled in the art, the BN inference employed by the learning process may be adapted for performing inference using uncertain evidence of one or more types, including likelihood evidence, probabilistic evidence, and/or any other type of uncertain evidence, and the learning process may invoke the BN inference for handling uncertainty of the corresponding type whenever it being encountered in the input data.

Moreover, any suitable learning algorithm which uses BN inference for calculating probabilities of random variables represented by the BN and then uses the resulting probabilities from the inference in updating of the estimate of the parameters of the BN may be employed in accordance with the disclosed subject matter to yield a learning process capable of incorporating uncertain data into the parameters' estimation.

In some embodiments, the learning process may also support integrating expert knowledge together with historical data, by incorporation thereof into the BN inference process being used thereby. Additionally or alternatively, continuous learning, i.e. continued updating of the parameters estimations or post-training of the model may be supported, for example, by calculating and saving the number of examples used to calculate each conditional probability distribution (CPD) entry, and using these values when updating the CPDs. Other enhancements that can be updated incrementally may similarly be incorporated during BN inference and by result in the learning process in whole, as can readily be appreciated by a person skilled in the art.

One technical effect of utilizing the disclosed subject matter is that parameter learning of a Bayesian network can be achieved also when the data provided or part of it being uncertain.

Another technical effect of utilizing the disclosed subject matter is incorporation of uncertain evidence in parameter learning of a Bayesian network at no additional significant cost.

Before explaining at least one embodiment in detail, it is to be understood that embodiments are not necessarily limited in its application to the details of construction and the arrangement of the components and/or methods set forth in the following description and/or illustrated in the drawings and/or the Examples. Implementations described herein are capable of other embodiments or of being practiced or carried out in various ways.

Embodiments may be a system, a method, and/or a computer program product. The computer program product may include a computer readable storage medium (or media) having computer readable program instructions thereon for causing a processor to carry out aspects of the embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments.

Aspects of embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1A, which is a schematic illustration of an exemplary Bayesian network, according to some embodiments. Reference is also made to FIG. 1B, which is a diagram of an exemplary conditional probability table of a node in a Bayesian network, according to some embodiments.

A Bayesian network (BN), such as BN 100 illustrated in FIG. 1A, may comprise a plurality of nodes, such as 110, 112 and 114, and a plurality of directed edges between pairs of nodes, such as edges 120 and 122 connecting nodes 110 and 112 to node 114 respectively. As shown in FIG. 1A, the BN 100 may depict a diagnosis network in the medical domain. The BN of FIG. 1A may also be known as the "Asia" network or "Lung cancer" network. Once its parameters have been determined, BN 100 may enable the use of evidence regarding "Visit to Asia?" together with "Smoker?", "Positive X-ray?", and "Dyspnoea?" to compute the probability of the "Lung cancer?", "Tuberculosis?" and "Bronchitis?" nodes.

An exemplary conditional probability table (CPT) of the node "Dyspnoea?" (node 114 of FIG. 1A) is shown in FIG. 1B. The left-most column in the CPT of FIG. 1B specifies the probability distribution or likelihood of Dyspnoea occurring or not given observations of both the nodes "Bronchitis?" and "Tuberculosis or Lung cancer?" (nodes 110 and 112 of FIG. 1A) being positive, where the top row corresponds to the node "Dyspnoea?" being positive and the bottom row to it being negative. Similarly, the second from left column in the CPT of FIG. 1B corresponds to probabilities of Dyspnoea occurring given that Bronchitis occurred and Tuberculosis or Lung cancer did not. The two right columns in the CPT of FIG. 1B similarly correspond to probabilities of Dyspnoea occurring given that Bronchitis did not occur and that Tuberculosis or Lung cancer occurred or not respectively.

As a person skilled in the can readily appreciate, it is quite conceivable that in real-world medical cases in which such diagnosis BNs need to be created, available historical information may be in unstructured format such as medical staff's written reports or X-ray images. For example, it is quite likely that whether or not a specific patient has the symptom "Dyspnoea?" or had a "Positive X-ray?" may have to be extracted from a written description documented by the physician examining this patient. NLP tools can be used to transform such unstructured data into a structured format with associated uncertainty. For example, an NLP tool run on such a historical report may be able to indicate with a 0.7 confidence level that a specific patient indeed had the "Dyspnoea?" symptom.

In a case such as this, where the result of an NLP analysis of a historical medical record indicates that in this record, the symptom "Dyspnoea?" occurred with 0.7 confidence, the information with uncertainty may be represented by assigning the node "Dyspnoea?" in the network the likelihood evidence (0.7; 0.3).

In accordance with some embodiments, inference in a BN given likelihood evidence can be carried out as follows: a virtual node for the observation may be added to the network with the appropriate CPT; the virtual evidence may be set as a hard finding on this node; and the evidence on all the nodes in the BN may then be propagated using standard BN propagation algorithms.

Figures 2A, 2B:
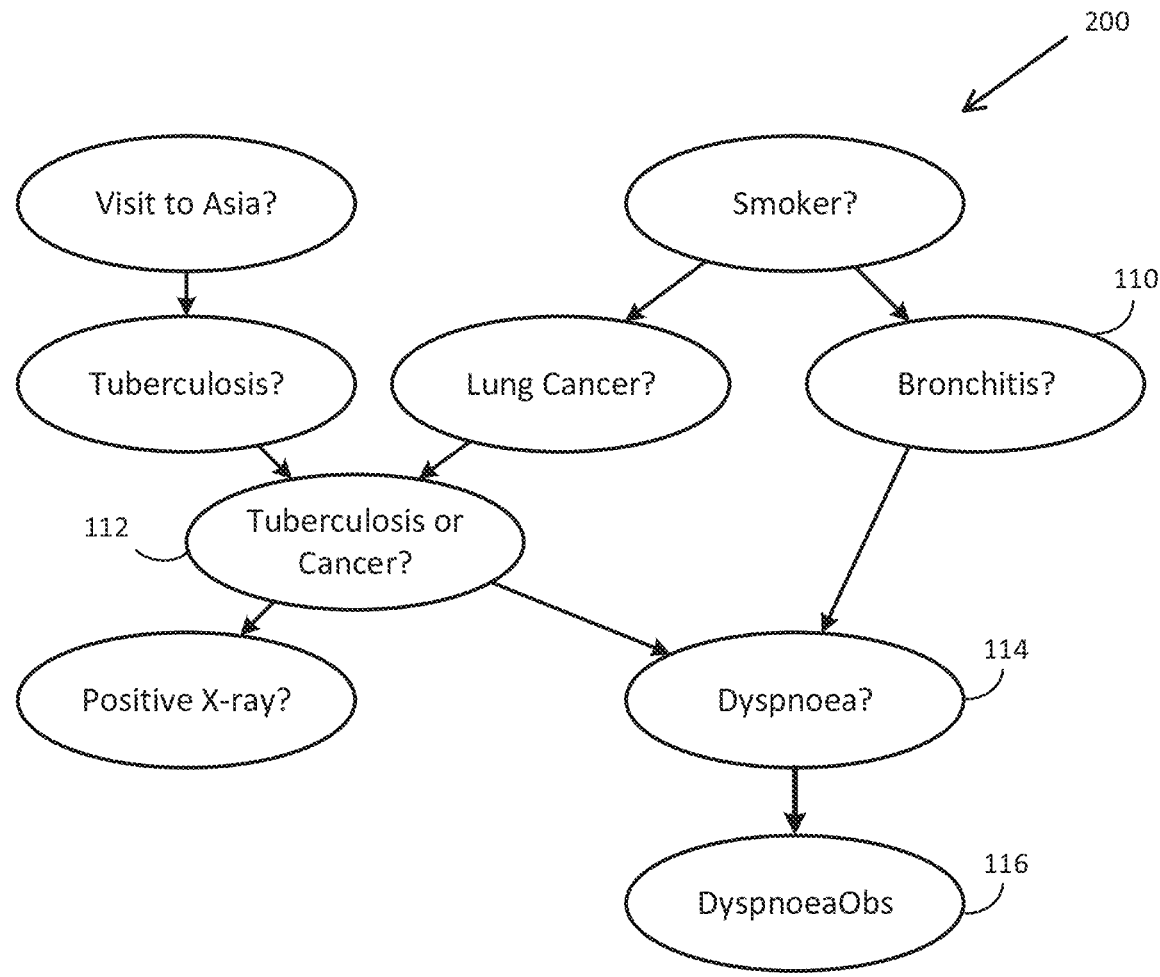
FIG. 2A is a schematic illustration of an exemplary Bayesian network augmented with a virtual node representing uncertain evidence, according to some embodiments.
FIG. 2B is a diagram of an exemplary conditional probability table of a virtual node in an augmented Bayesian network, according to some embodiments.

Reference is now made to FIG. 2A, which is a schematic illustration of an exemplary Bayesian network augmented with a virtual node representing uncertain evidence, according to some embodiments. Reference is also made to FIG. 2B, which is a diagram of an exemplary conditional probability table of a virtual node in an augmented Bayesian network, according to some embodiments.

Referring now to FIG. 2A, augmented BN 200 may consist of nodes and edges of BN 100 of FIG. 1A, such as nodes 110, 112 and 114 and edges 120 and 122. In addition, augmented BN 200 may comprise for each node with likelihood evidence a child node representing the observed value with uncertainty of the node, along with corresponding CPT for the child node with probabilities matching the likelihoods of each of the possible values of its parent node.

For example, as shown in FIG. 2A, the original "Asia" BN 100 of FIG. 1A may be extended with a boolean (true/false) node "DyspnoeaObs", such as node 116, added to BN 100 as a child of "Dyspnoea?" (node 114), thus yielding augmented BN 200. The node 116 may then have the CPT given in FIG. 2B associated with it. The value of "DyspnoeaObs" may be set to "true" accordingly, and inference may be carried out on the augmented BN 200 using any standard BN inference algorithm.

Figure 3:
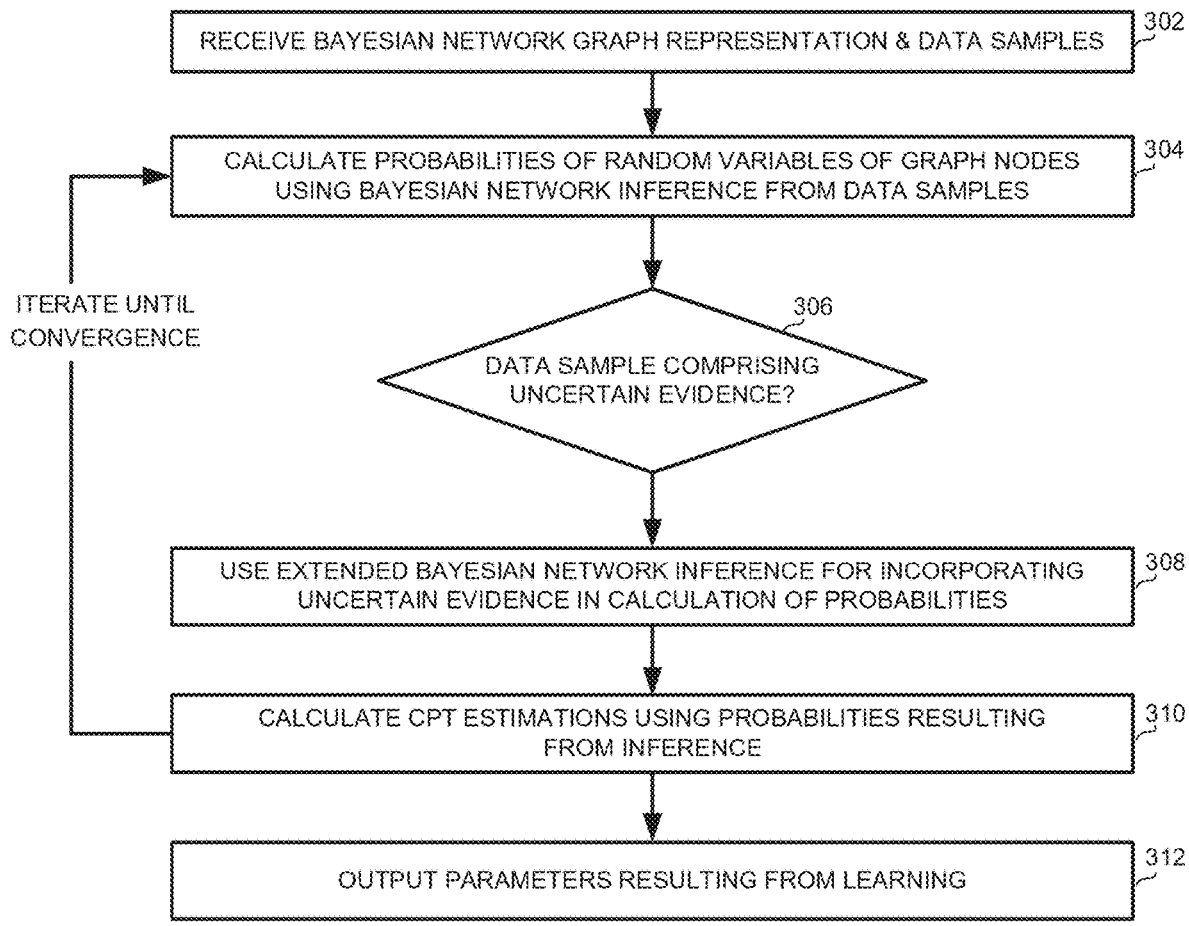
FIG. 3 is a flowchart of a method for learning parameters of Bayesian network given uncertain evidence, according to some embodiments.

Reference is now made to FIG. 3, which is a flowchart of a method for learning parameters of Bayesian network given uncertain evidence, according to some embodiments.

At 302 an input comprising a graph representation and one or more data samples of a Bayesian network may be received. The graph of the Bayesian network may comprise a plurality of nodes representing random variables and a plurality of directed edges between pairs of nodes representing conditional dependencies among respective variables represented thereby. In some embodiments, the received data samples may comprise known, missing, and/or uncertain values for each of the plurality of random variables nodes. In some further embodiments, the uncertain values may be associated with a likelihood ratio and/or a probability distribution over a domain of possible values of the respective nodes for which the uncertain values being observed in a corresponding sample.

At 304 probabilities of the plurality of random variables represented by the nodes of the Bayesian network graph received at 302 may be calculated using a Bayesian network inference process and the data samples received at 302.

At 306 a determination may be made as to whether a received data sample comprises uncertain evidence, for example, an uncertain value for a node with associated probability distribution and/or likelihood ratio.

At 308 if the determination made at 306 being to the affirmative, the uncertain evidence may be accordingly incorporated in the calculation of probabilities through use of an uncertainty Bayesian network inference process adapted for this task. For example, in case of likelihood evidence encountered in a sample, the received Bayesian network may be augmented with a virtual node and corresponding conditional probability table (CPT) for each node with an observed uncertain value, and inference may be performed on the augmented network using standard propagation methods. Similarly, in case of probabilistic evidence for which there may be at hand an appropriate inference method of incorporating the uncertain information in the propagation throughout the Bayesian network, such uncertainty inference process may be used with the uncertain data. A review of exemplary techniques and tools for propagating probabilistic evidence in a Bayesian network, i.e. inference from data comprising probabilistic evidence, is found in Mrad et al., for example. It will be appreciated that the probabilistic evidence may comprise a probability distribution over values of a single node or a set of nodes (i.e. a joint distribution), and may be affectable by additional information on the network (i.e. not-fixed) or not affectable thereby (i.e. fixed probabilistic evidence).

At 310, CPT estimations for the Bayesian network received at 302 may be calculated using the probabilities resulting from the inference performed at 304 through 306 and 308.

In some embodiments, the learning process from 304 to 310 may be iterated for a number of times until convergence.

At 312 the parameters of the Bayesian network resulting from the learning process of 304 to 310, i.e. the CPTs calculated for the plurality of graph nodes, may be outputted. Optionally a number of the data samples used in calculation of the CPTs, e.g. the number of data samples received at 302, may be recorded and stored, to enable implementation of continuous learning scheme, wherein probability distribution entry may be updated using the number of data samples as stored.

Reference is now made to FIG. 4 which is a pseudo-code of an exemplary Expectation-Maximization algorithm for learning parameters of a Bayesian network using likelihood evidence.

According to some embodiments, an algorithm such as shown in FIG. 4, also referred to herein as "EM-likelihood" algorithm, may take as input a Bayesian network $\mathcal{B} = \langle X, D, G, P \rangle$ with graph $G = \langle \mathbb{V}, \mathbb{E} \rangle$, where $\mathbb{V}$ is the set of nodes corresponding to the discrete variables X and $\mathbb{E}$ is the set of edges in the network, and a set of data examples S. Each data example $S_j \in S$ may contain one element $d_V \in \text{domain}(V) \cup \{?\} \cup \{l_V\}$ for each $V \in \mathbb{V}$, where "?" denotes an unknown value and $\{l_V\}$ is likelihood evidence for node V. For each node V with k possible values for which likelihood evidence $l_V$ is provided, $l_V$ consists of numbers $\{\Pr(\text{obs}|V=v_1), \ldots, \Pr(\text{obs}|V=v_k)\}$. That is, for each data item $S_j$, the value for variable V can be any of its discrete values, unknown, or a new type of value, indicating likelihood evidence.

In the algorithm pseudo-code of FIG. 4, $o_V$ denotes the node for which $d_V$ is an observation in $S_j$, and $O_j$ denotes the set of variables in $S_j$ for which there is likelihood evidence. Further, Conf in the algorithm are the actual likelihood values provided for a node. Also, θ is used to denote the network's parameters, i.e., the set of all entries of the CPTs in P. Furthermore, $θ^t$ represents the parameters of the network in iteration t of the algorithm (the initial values for θ may be uniformly sampled or otherwise determined as an educated guess).

As shown in FIG. 4, the EM-Likelihood algorithm may extend the original Bayesian network (BN) with nodes specific to each example that contains likelihood evidence, in order to enable inference with likelihood evidence during the expectation step. This step is carried out in the function AUGMENT-BN.

In FIG. 4, the term $\text{Val}(X_i, Pa_{X_i}^{\mathcal{B}})$ is used to denote the joint set of possible values of a node $X_i$ and its parents $Pa_{X_i}^{\mathcal{B}}$, in $\mathcal{B}$. The term $d_j$ is used to denote the union of known values in example $S_j$ and the evidence obtained by setting to "true" the auxiliary nodes, performed after the function AUGMENT-BN returns the augmented network G'. The joint marginals $P_{(G', θ^t)}(x_i, u_i | d_j)$ are obtained via inference in the augmented network G'. The term $M_{θ^t}[u]$ denotes the sum $\Sigma_{x_i} M_{θ^t}[x_i, u_i]$.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and methods for learning parameters of Bayesian network using uncertain evidence will be developed and the scope of the term uncertainty learning is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment may include a plurality of "optional" features unless such features conflict.

Throughout this application, various embodiments may be presented in a range format. It should be understood that the description in range format is merely for convenience and brevity and should not be construed as an inflexible limitation on the scope of embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of embodiments, which are, for clarity, described in the context of separate embodiments, may also be provided in combination in a single embodiment. Conversely, various features of embodiments, which are, for brevity, described in the context of a single embodiment, may also be provided separately or in any suitable subcombination or as suitable in any other described embodiment. Certain features described in the context of various embodiments are not to be considered essential features of those embodiments, unless the embodiment is inoperative without those elements.

Although embodiments have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for learning parameters of Bayesian network from uncertain evidence, comprising:
   receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value comprising an observed value and associated confidence level between 0 and 1; wherein the at least one sample comprising one or more uncertain values in one or more samples;
   applying on the input Bayesian network learning comprising:
      inferring probabilities of random variables represented by the plurality of nodes, by applying on the input Bayesian network uncertain inference comprising performing inference in the Bayesian network from the at least one sample comprising the one or more uncertain values in the one or more samples; and
      calculating estimates of conditional probability tables of the Bayesian network using the probabilities inferred; and
   performing a machine learning based task using the estimates of conditional probability tables calculated.

2. The method of claim 1, wherein for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; and a likelihood ratio comprising quantitative representation of a conditional probability of an observed value of the node in the sample for each value in a domain of possible values of the node.

3. The method of claim 2, wherein the Bayesian network uncertain inference further comprises obtaining an augmented Bayesian network by adding a child node and corresponding conditional probability table for each node of the at least one node being associated with a likelihood ratio, the child node representing a binary random variable of whether for the node the uncertain value being observed in the sample, the corresponding conditional probability table comprising probabilities obtained from the likelihood ratio, and wherein the uncertain Bayesian network inference further comprises performing inference using the augmented Bayesian network and known values of the sample.

4. The method of claim 1, wherein the Bayesian network uncertain inference further comprises completing a sample comprising at least one unknown value by calculating a statistic for each node for which the value thereof in the sample being unknown.

5. The method of claim 1, wherein the Bayesian network learning further comprises iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

6. The method of claim 1, wherein the Bayesian network learning further comprises performing continuous learning by calculating and saving a number of samples used for calculating each of at least one probability distribution entry in a conditional probability table of the Bayesian network, and updating each of the at least one probability distribution entry using the number of samples saved.

7. The method of claim 1, wherein the Bayesian network learning further comprises incorporating expert estimates.

8. A computer program product comprising:
   a non-transitory computer readable storage medium;
   program instructions for executing, by a processor, a method for learning parameters of Bayesian network from uncertain evidence, the method comprising:
      receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value comprising an observed value and associated confidence level between 0 and 1; wherein the at least one sample comprising one or more uncertain values in one or more samples;
      applying on the input a Bayesian network learning comprising:
         inferring probabilities of random variables represented by the plurality of nodes, by applying on the input Bayesian network uncertain inference comprising performing inference in the Bayesian network from the at least one sample comprising the one or more uncertain values in the one or more samples-; and
         calculating estimates of conditional probability tables of the Bayesian network using the probabilities inferred; and
      performing a machine learning based task using the estimates of conditional probability tables calculated.

9. The computer program product of claim 8, wherein for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; and a likelihood ratio comprising quantitative representation of a conditional probability of an observed value of the node in the sample for each value in a domain of possible values of the node.

10. The computer program product of claim 9, wherein the Bayesian network uncertain inference further comprises obtaining an augmented Bayesian network by adding a child node and corresponding conditional probability table for each node of the at least one node, the child node representing a binary random variable of whether for the node the uncertain value being observed in the sample, the corresponding conditional probability table comprising probabilities obtained from the likelihood ratio, and wherein the Bayesian network uncertain inference further comprises performing inference using the augmented Bayesian network and known values of the sample.

11. The computer program product of claim 8, wherein the Bayesian network uncertain inference further comprises completing a sample comprising at least one unknown value by calculating a statistic for each node for which the value thereof in the sample being unknown.

12. The computer program product of claim 8, wherein the Bayesian network learning further comprises iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

13. The computer program product of claim 8, wherein the Bayesian network learning further comprises performing continuous learning by calculating and saving a number of samples used for calculating each of at least one probability distribution entry in a conditional probability table of the Bayesian network, and updating each of the at least one probability distribution entry using the number of samples saved.

14. The computer program product of claim 8, wherein the Bayesian network learning further comprises incorporating expert estimates.

15. A system for learning parameters of Bayesian network from uncertain evidence, comprising:
 a processing circuitry adapted to execute a code for:
  receiving an input comprising graph representation and at least one sample of a Bayesian network, wherein the graph comprising a plurality of nodes representing random variables and a plurality of directed edges between pairs of nodes from the plurality of nodes representing conditional dependencies, wherein each of the at least one sample comprising for each node of the plurality of nodes a value selected from the group consisting of: a known value; an unknown value; and an uncertain value comprising an observed value and associated confidence level between 0 and 1; wherein the at least one sample comprising one or more uncertain values in one or more samples;
  applying on the input a Bayesian network learning comprising:
   inferring probabilities of random variables represented by the plurality of nodes, by applying on the input Bayesian network uncertain inference comprising performing inference in the Bayesian network from the at least one sample comprising the one or more uncertain values in one or more samples-; and
   calculating estimates of conditional probability tables of the Bayesian network using the probabilities inferred; and
  performing a machine learning based task using the estimates of conditional probability tables calculated.

16. The system of claim 15, wherein for at least one node for which the value in a sample of the at least one sample being uncertain, each of the at least one node being associated with at least one of: a probability distribution over a domain of possible values of at least a subset of the at least one node comprising one or more nodes, wherein the probability distribution being either affectable or not affectable by additional information on the Bayesian network; probability distribution being either affectable or not affectable by additional information on the Bayesian network; and a likelihood ratio comprising quantitative representation of a conditional probability of an observed value of the node in the sample for each value in a domain of possible values of the node.

17. The system of claim 16, wherein the Bayesian network uncertain inference further comprises obtaining an augmented Bayesian network by adding a child node and corresponding conditional probability table for each node of the at least one node being associated with a likelihood ratio, the child node representing a binary random variable of whether for the node the uncertain value being observed in the sample, the corresponding conditional probability table comprising probabilities obtained from the likelihood ratio, and wherein the Bayesian network uncertain inference further comprises performing inference using the augmented Bayesian network and known values of the sample.

18. The system of claim 15, wherein the Bayesian network uncertain inference further comprises completing a sample comprising at least one unknown value by calculating a statistic for each node for which the value thereof in the sample being unknown.

19. The system of claim 15, wherein the Bayesian network learning further comprises iteratively calculating for each sample of the at least one sample an expected value for each node which value thereof in the sample being unknown using estimates of conditional probability tables of the Bayesian network, and updating estimates of conditional probability tables of the Bayesian network by calculating a maximum likelihood estimator using the at least one sample and expected values calculated therefor.

20. The system of claim 15, wherein the Bayesian network learning further comprises performing continuous learning by calculating and saving a number of samples used for calculating each of at least one continuous probability distribution entry in a conditional probability table of the Bayesian network, and updating each of the at least one continuous probability distribution using the number of samples saved.

21. The system of claim 15, wherein the Bayesian network learning further comprises incorporating expert estimates.

* * * * *